United States Patent
Weaver

(10) Patent No.: US 9,964,741 B2
(45) Date of Patent: *May 8, 2018

(54) TELECENTRIC LENS ASSEMBLY PROVIDING A COLLIMATED LIGHT SPACE

(71) Applicant: Vanderbilt University, Nashville, TN (US)

(72) Inventor: Charles David Weaver, Franklin, TN (US)

(73) Assignee: Vanderbilt University, Nashville, TN (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/370,669

(22) Filed: Dec. 6, 2016

(65) Prior Publication Data
US 2017/0082836 A1    Mar. 23, 2017

Related U.S. Application Data

(63) Continuation of application No. 14/173,290, filed on Feb. 5, 2014, now Pat. No. 9,513,470.
(Continued)

(51) Int. Cl.
| | |
|---|---|
| *G02B 13/22* | (2006.01) |
| *G02B 3/00* | (2006.01) |
| *G02B 21/00* | (2006.01) |
| *G02B 21/36* | (2006.01) |
| *G02B 21/16* | (2006.01) |
| *G06T 11/60* | (2006.01) |
| *G02B 7/00* | (2006.01) |
| *G02B 13/00* | (2006.01) |

(Continued)

(52) U.S. Cl.
CPC .......... *G02B 13/22* (2013.01); *G02B 3/0068* (2013.01); *G02B 7/006* (2013.01); *G02B 13/006* (2013.01); *G02B 21/008* (2013.01); *G02B 21/16* (2013.01); *G02B 21/367* (2013.01); *G02B 27/106* (2013.01); *G02B 27/141* (2013.01); *G02B 27/30* (2013.01); *G06T 11/60* (2013.01); *B01L 3/5085* (2013.01); *G01N 21/253* (2013.01); *G01N 21/6452* (2013.01)

(58) Field of Classification Search
CPC ...................................................... G02B 13/22
See application file for complete search history.

(56) References Cited

U.S. PATENT DOCUMENTS

| | | | |
|---|---|---|---|
| 6,292,306 B1 * | 9/2001 | Betensky | G02B 13/22 359/663 |
| 6,674,510 B1 * | 1/2004 | Jasper | G03F 9/70 355/53 |

(Continued)

*Primary Examiner* — Casey Bryant
(74) *Attorney, Agent, or Firm* — Tarolli, Sundheim, Covell & Tummino LLP

(57) ABSTRACT

Systems and methods for imaging a target are provided. A system includes a detector and a substantially bitelecentric lens assembly positioned between the detector and the target. A first optical assembly is configured to focus light received from the substantially bitelecentric lens assembly onto the detector. The substantially bitelecentric lens assembly and the first optical assembly are configured to produce a collimated light space between the substantially bitelecentric lens assembly and the first optical assembly. A second optical assembly is positioned within the collimated light space.

20 Claims, 2 Drawing Sheets

Related U.S. Application Data

(60) Provisional application No. 61/760,976, filed on Feb. 5, 2013.

(51) Int. Cl.
    *G02B 27/10*    (2006.01)
    *G02B 27/14*    (2006.01)
    *G02B 27/30*    (2006.01)
    *B01L 3/00*    (2006.01)
    *G01N 21/25*    (2006.01)
    *G01N 21/64*    (2006.01)

(56) References Cited

U.S. PATENT DOCUMENTS

| | | | |
|---|---|---|---|
| 9,513,470 B1 * | 12/2016 | Weaver | G02B 13/22 |
| 2004/0106217 A1 | 6/2004 | Higgs | |
| 2013/0308199 A1 | 11/2013 | Shiue | |
| 2014/0104604 A1 | 4/2014 | Ahner et al. | |

* cited by examiner

TELECENTRIC LENS ASSEMBLY PROVIDING A COLLIMATED LIGHT SPACE

CROSS-REFERENCE TO RELATED APPLICATIONS

This application is a continuation of U.S. application Ser. No. 14/173,290, filed on Feb. 5, 2014, which is now U.S. Pat. No. 9,513,470, issued Dec. 6, 2016, which claims priority to U.S. Provisional Patent Application No. 62/760,976, filed Feb. 5, 2013. The content of both are hereby incorporated by reference herein.

TECHNICAL FIELD

This invention relates to imaging systems, and more particularly, to use of a telecentric lens assembly providing a collimated light space.

BACKGROUND

A telecentric lens is a compound lens which has its entrance or exit pupil at infinity. In other words, the chief rays, that is, oblique rays which pass through the center of the aperture stop, are parallel to the optical axis in front of or behind the system, respectively. An entrance pupil at infinity makes the lens object-space telecentric. Such lenses are used in machine vision systems because image magnification is independent of the object's distance or position in the field of view, referred to as an orthographic view. An exit pupil at infinity makes the lens image-space telecentric.

SUMMARY OF THE INVENTION

In accordance with an aspect of the present invention, an imaging system includes a detector and a substantially bitelecentric lens assembly positioned between the detector and the target. A first optical assembly is configured to focus light received from the substantially bitelecentric lens assembly onto the detector. The substantially bitelecentric lens assembly and the first optical assembly are configured to produce a collimated light space between the substantially bitelecentric lens assembly and the first optical assembly. A second optical assembly is positioned within the collimated light space.

In accordance with another aspect of the present invention, a method is provided for imaging a target in accordance with an aspect of the present invention. A target is aligned in a field of view of an object-side telecentric lens assembly having a first auxiliary optical element in a collimated light space. The target is imaged using the first optical element with an imaging system associated with the telecentric lens. A second auxiliary optical element is exchanged for the first auxiliary optical element without disturbing the alignment of the target at the telecentric lens. The target is then imaged using the second auxiliary optical element with the image system.

In accordance with yet another aspect of the present invention, a kinetic imaging plate reader system is provided. The system includes a detector and a lens assembly positioned between the detector and a microplate. An optical assembly is configured to focus light received from the lens assembly onto the detector. The lens assembly and the first optical assembly are configured to produce a collimated light space between the lens assembly and the first optical assembly. A first filter is positioned within the collimated light space. The first filter is configured to be modular, such that the first filter can be removed and replaced with a second filter without substantial disturbance of any of the detector, the lens assembly, and the optical assembly.

DETAILED DESCRIPTION

Figure 1:
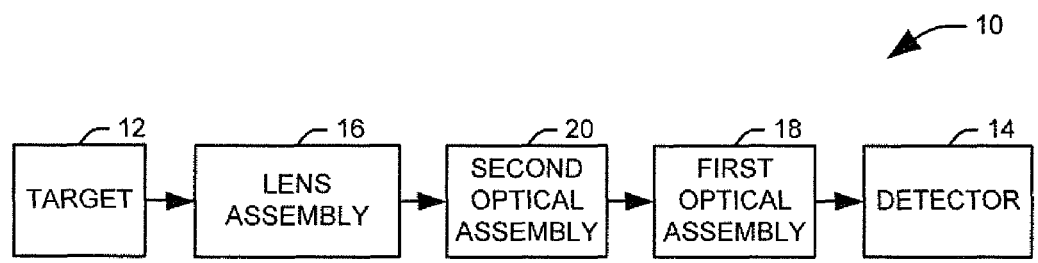
FIG. 1 illustrates a system for imaging a target in accordance with an aspect of the present invention.

FIG. 1 illustrates a system 10 for imaging a target 12 in accordance with an aspect of the present invention. The system 10 includes a detector 14 and a substantially bitelecentric lens assembly 16 positioned between the detector 14 and the target 12. The substantially bitelecentric lens assembly 16 is configured to have an entrance pupil at an infinite distance from the lens, and an exit pupil that is a significant distance from the lens, such that the chief rays of light emitted from the lens assembly 16 are substantially parallel to an optical axis of the system. By "substantially parallel," it is meant that the chief rays form an angle no greater than fifteen degrees with the optical axis. By "substantially bitelecentric," it is meant that the chief rays of light entering and emitted from the lens are substantially parallel to the optical axis of the system.

A first optical assembly 18 is positioned between the substantially bitelecentric lens assembly 16 and the target 14. The first optical assembly 18 is configured to focus light from the substantially bitelecentric lens assembly 16 onto the detector 14, such that an image plane of the substantially bitelecentric lens assembly falls between the lens assembly and the first optical assembly 18. It will be appreciated that, in accordance with an aspect of the present invention, the chief rays of light emitted from the lens assembly 16 are substantially parallel for at least a portion of the region between the bitelecentric lens assembly and the first optical assembly 18. In one implementation, the first optical assembly 18 can be a substantially object-space telecentric lens assembly configured to receive the substantially parallel light rays from the substantially bitelecentric lens assembly 16 onto the detector 14. By "substantially object-space telecentric," it is meant that the chief rays of light entering the optical assembly are substantially parallel to the optical axis of the system.

To this end, a second optical assembly 20 can be positioned between the substantially bitelecentric lens assembly 16 and the first optical assembly 18, such that the second optical assembly 20 is within the region for which the chief rays of light emitted from the substantially bitelecentric lens assembly 16 are substantially parallel, a collimated light space. In one implementation, the second optical assembly 20 can include one of a filter, a dichroic mirror, and a beam splitter. In one implementation, the second optical assembly 20 can be one of a set of standard, off-the-shelf emission filters configured in a high-speed rotary filter wheel to allow for rapid switching of filters into the collimated light space. These filters can include, for example, any of spectral filters, such as longpass filters, shortpass filters, neutral density filters, polarizers, and dichroic filters. In one implementation, the collimated light space could also accommodate a micro-filter array (MFA) for multispectral or hyperspectral imaging. This could be a pixel-matched MFA that is fixed within the collimated space or a coarser array, for example, with elements corresponding to three-pixel by three-pixel blocks to the aperture of a microlens array and translated rapidly within a plane parallel to the optical axis with an actuator, such as a piezoelectric actuator. In another implementation, the second optical assembly 20 can be a microlens array, a micropolarizer array, a micro-prism array, and a micro-diffraction grating array In one implementation, the system 10 is part of a kinetic imaging plate reader system, and the target 12 is a microplate. In this implementation, the collimated light space can be used, for example, to enable rapid switching of commercially available filters with restrictive design specifications. Such a system could further include an automated liquid handling system configured to dispense liquid into a plurality of wells in the microplate. Accordingly, the microplate could positioned above each of the detector 14, the substantially bitelecentric lens assembly 16, and the first optical assembly 18 such that the microplate is freely accessible to the automated liquid handling system. It will further be appreciated that the imaging system could be configured for use with any of visible light, infrared light, ultraviolet light, and microwave radiation as well. For example, while the plate reader might be configured to detect visible light, in one implementation, the target 12 might be an integrated circuit, and the system might be part of an integrated circuit testing assembly. In such a case, the lens assembly 16 might be configured to image within the infrared band. A non-exhaustive list of other applications can include next generation sequencing applications, protein and nucleic acid microarray analysis, electrophorectic gel and blot analysis, and whole animal imaging.

Figure 2:
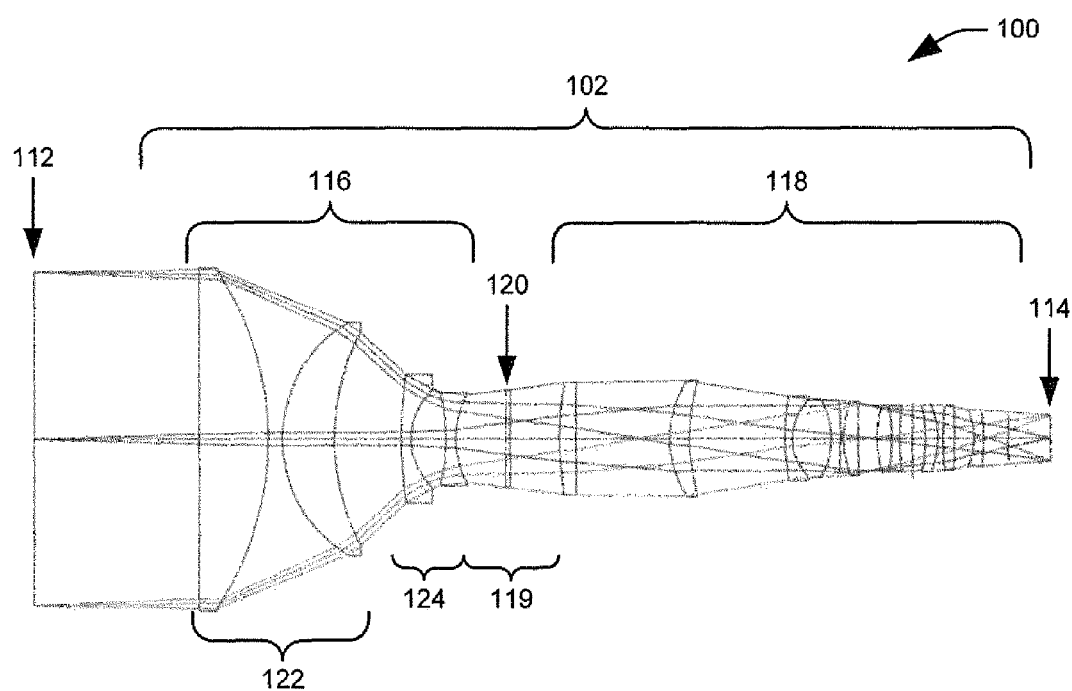
FIG. 2 illustrates one implementation of a system for imaging a target in accordance with an aspect of the present invention.

FIG. 2 illustrates an imaging system 100 incorporating a lens arrangement 102 designed specifically to have a high light gathering ability and to produce an essentially distortion-free image of a target 112. In the illustrated implementation, the target 112 can have a height of about one hundred thirty-six millimeters, and the lens arrangement 102 can be positioned about 67.6 millimeters from the target, and have an overall length, along its optical axis, of approximately 330.2 millimeters. A detector 114 is configured to collect light from the lens arrangement 102. In the illustrated implementation, the detector has a diagonal dimension of around 18.8 millimeters.

In accordance with an aspect of the present invention, there is a collimated light space 119 in the lens arrangement 102 where the light rays have been made substantially parallel with the long axis of the lens allowing optical elements 120 to be placed within the lens in a way that preserves their ability to perform within their design specifications. For example, elements such as filters and dichroic mirrors can require that light incident on the element have a specific angle of incidence and using these filters or mirrors outside of the limits of their design specifications can significantly degrade the performance of the element. Accordingly, the element 120 can include relatively small, low mass, commercially available filters to be incorporated into a high-sensitivity, distortion-free optical train producing very flexible, versatile, and very high-performing imaging system 100 that is superior to what is presently used in plate-based imagers.

The lens arrangement 102 includes a substantially bitelecentric lens assembly 116 configured to collect light from the target 112 and provide the light aligned appropriately for the collimated light space 119 associated with the optical element 120. In the illustrated implementation, the substantially bitelecentric lens assembly 116 includes two doublet lens sets 122 and 124. A first doublet lens set 122 includes a plano-convex lens, with the planar side oriented toward the microplate target 112, and a positive meniscus lens, with the concave side oriented toward the second doublet lens set 124. The second doublet lens set 124 includes a negative meniscus lens, with the convex side oriented toward the first doublet lens assembly 122, and a biconcave lens. The light rays leaving the second doublet lens assembly 124 are substantially parallel with an optical axis of the lens arrangement 102.

The lens arrangement 102 further includes a substantially object-space telecentric lens assembly 118, separated from the substantially bitelecentric lens assembly 116 by the collimated light space 119. In the illustrated implementation, the distance between the substantially bitelecentric lens assembly 116 and the substantially object-space telecentric lens assembly 118, and thus the length of the collimated light space 119, is around 37.8 millimeters. A height of the collimated light space 119, and thus an approximate height of the lens assemblies 116 and 118 at the point closest to the collimated light space 119, is around forty-six millimeters. The substantially object-space telecentric lens assembly 118 focuses light from the collimated light space onto the detector 114. Taken as a whole, the lens arrangement 102 provides a large format, high light-gathering (e.g., a focal ratio on the order of F/1.78) object-side telecentric lens with a filter-friendly collimated space 119 for filters and other optical components with limited design specifications.

In accordance with an aspect of the present invention, the optical element 120 can be part of a set of multiple excitation and emission filters selected to support a broad ranging of fluorescent probes as well as fluorescence polarization, fluorescence resonance energy transfer (FRET), and bioluminescence resonance energy transfer (BRET) that can be readily swapped into the collimated light space 119. For example, the filters can include a filter set appropriate for blue fluorescent protein (BFP), a filter set appropriate for red fluorescent protein (RFP), and a filter set appropriate for green calcium or thallium-sensitive fluorescent dye.

It will be appreciated that the object-side telecentric lens arrangement 102 of the current invention provides a number of advantages, including a constant level of magnification, low distortion, and cancellation of perspective effects. In addition, the collimated light space 119 allows for rapidly changing of filters and other optical components for different kinds of contrast, polarization, and off-axis light introduction. All of these properties are useful for applications such as machine vision, metrology, and astronomy.

The ability to change filters can also be useful for multicolor imaging in gene sequencing, as well as multicolor imaging with whole animals or large pathology sections. In addition, the lens arrangement 102 has very high light-gathering (e.g., a focal ratio on the order F/1.8 as opposed to F/12-16 for existing telecentric lens designed for industrial machine vision applications), and a relatively narrow depth of field. High light gathering is important for low-light imaging in microplates, and the narrow depth of field is important for some amount of out-of-focus light rejection. In microplate imaging, the target may be a thin cell layer on the bottom of a plate covered by fluorescent fluid, making this out-of-focus rejection useful for avoiding spurious results. Finally, the combination of telecentricity, low light gathering, and filter changing is useful for gel imaging systems where multiple fluorescent antibodies are used to label proteins electrophoretically separated on a gel.

Figure 3:
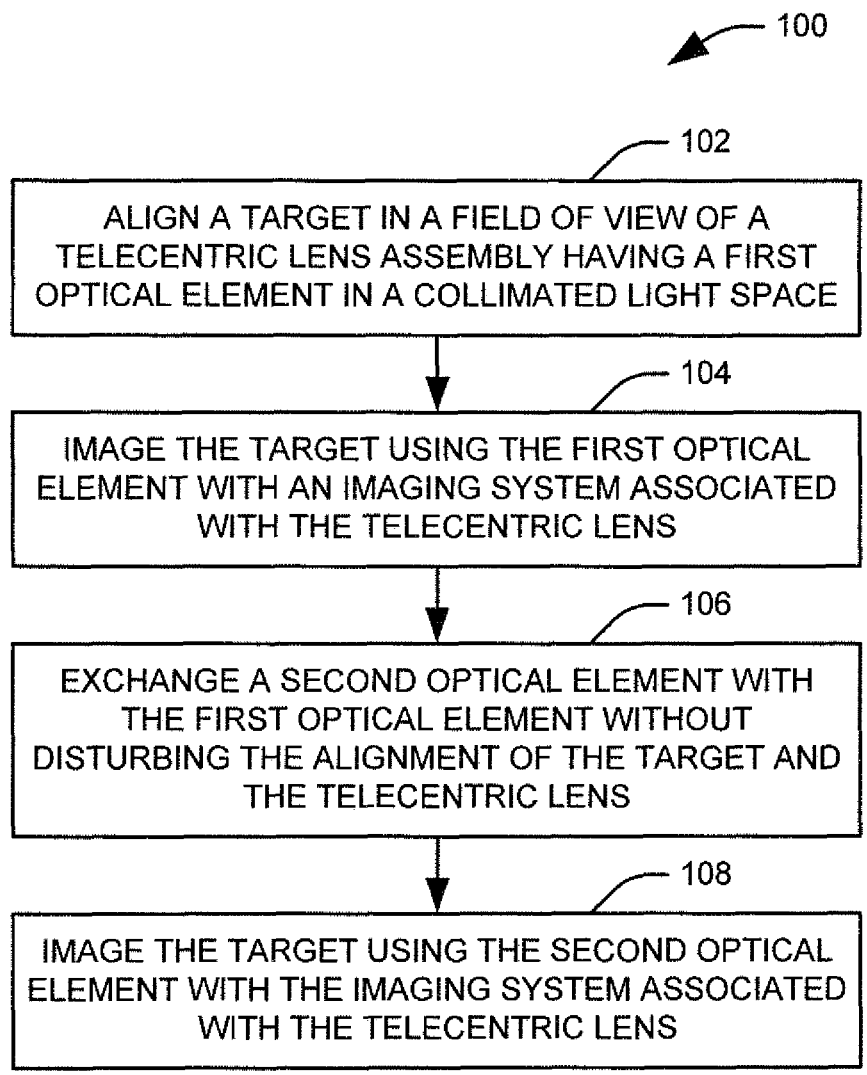
FIG. 3 illustrates a method for imaging a target in accordance with an aspect of the present invention.

In view of the foregoing structural and functional features described above, a methodology in accordance with various aspects of the present invention will be better appreciated with reference to FIG. 3. While, for purposes of simplicity of explanation, the methodology of FIG. 3 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 3 illustrates a method 100 for imaging a target in accordance with an aspect of the present invention. At 102, a target is aligned in a field of view of an object-side telecentric lens assembly having a first auxiliary optical element in a collimated light space. By a "collimated light space," it is meant a region of the optical train of the lens assembly in which the chief light rays are substantially parallel. In one implementation, the object-side telecentric lens assembly has a focal ratio less than F/2. At 104, the target is imaged using the first optical element with an imaging system associated with the telecentric lens. At 106, a second auxiliary optical element is exchanged for the first auxiliary optical element without disturbing the alignment of the target at the telecentric lens. At 108, the target is imaged using the second auxiliary optical element with the image system.

Many optical elements, such as filters, beam splitters, and dichroic mirrors, have relatively tight design tolerances, and will not function properly if the angle of incidence of incoming light is too great. Accordingly, it is often necessary to utilized specialized elements at fixed locations within the optical train to provide these functions. Because the collimated light space is compatible with the design specification of these components, they can be exchanged freely, without disturbing the lens assembly or the alignment of the lens assembly with the target. In one implementation, the optical assemblies can be microfilter arrays. In another implementation, the first and second auxiliary optical elements are filters on a high-speed rotary filter wheel. In this case, the optical elements can be exchanged without disturbing the alignment by rotating the high-speed rotary filter wheel.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. An imaging system comprising:
   a detector;
   a lens assembly, positioned between the detector and a target;
   a first optical assembly configured to focus light received from the lens assembly onto the detector, the lens assembly and the first optical assembly being configured to produce a collimated light space between the lens assembly and the first optical assembly; and
   a beam splitter positioned within the collimated light space.

2. The imaging system of claim 1, wherein the lens assembly is substantially image-space telecentric.

3. The imaging system of claim 1, wherein the beam splitter comprises a polychroic mirror.

4. The imaging system of claim 3, wherein the polychroic mirror comprises a bichroic mirror.

5. The imaging system of claim 4, wherein the second optical assembly is at least one of a microfilter array, a microlens array, a micropolarizer array, a micro-prism array, and a micro-diffraction grating array.

6. The imaging system of claim 4, wherein the second optical assembly is one of a longpass filter, a shortpass filter, a neutral density filter, a polarizer, and a dichroic filter.

7. The imaging system of claim 1, further comprising a second optical assembly positioned within the collimated light space.

8. The imaging system of claim 7, wherein the second optical assembly is configured to be modular, such that the second optical assembly can be removed and replaced with a third optical assembly without disturbance of the detector, the lens assembly, and the first optical assembly.

9. The imaging system of claim 8, wherein each of the second optical assembly and the third optical assembly comprise at least one filter configured in a filter changer.

10. The imaging system of claim 1, wherein the target is an integrated circuit and the imaging system is part of an integrated circuit testing system.

11. The imaging system of claim 1, wherein the target is a microplate, and the imaging system is part of a plate reader.

12. The imaging system of claim 1, wherein a lens arrangement comprising the first lens assembly and the first optical assembly has a focal ratio less than F/2.

13. The imaging system of claim 1, wherein the at least one of the dichroic mirror and a beam splitter is configured to be modular, such that the at least one of the dichroic mirror and a beam splitter can be removed and replaced with another beam splitter or dichroic mirror without disturbance of the detector, the lens assembly, and the first optical assembly.

14. A method for imaging a target comprising:
   aligning a target in a field of view of lens assembly having a filter in a collimated light space;
   imaging the target using the filter with an imaging system associated with the lens assembly;
   exchanging a second filter for the first filter without disturbing the alignment of the target at the lens assembly; and
   imaging the target using the second filter with the image system.

15. The method of claim 14, wherein the first and second filters are deployed on a filter changer, and exchanging the second filter for the first filter without disturbing the alignment of the target at the lens assembly comprises activating the filter changer.

16. The method of claim 14, wherein the lens assembly has a focal ratio less than F/2.

17. A plate reader system comprising:
   a detector;
   a lens assembly, positioned between the detector and a microplate;
   an optical assembly configured to focus light received from the lens assembly onto the detector, the lens assembly and the first optical assembly being configured to produce a collimated light space between the lens assembly and the first optical assembly;
   at least one of a dichroic mirror and a beam splitter positioned within the collimated light space; and a first filter positioned within the collimated light space, the first filter being configured to be modular, such that the first filter can be removed and replaced with a second filter without substantial disturbance of any of the detector, the lens assembly, and the optical assembly.

18. The plate reader system of claim 17, further comprising an automated liquid handling system configured to dispense liquid into a plurality of wells in the microplate.

19. The plate reader system of claim 18, wherein the microplate is positioned above each of the detector, the lens assembly, and the optical assembly such that the microplate is freely accessible to the automated liquid handling system.

20. The plate reader system of claim 17, wherein the first and second filters are part of a set of excitation and emission filters selected to support fluorescent probes, the set of filters including at least one filter configured to selectively passing light from blue fluorescent protein, at least one filter configured to selectively passing light from red fluorescent protein, and at least one filter configured to selectively passing light from one of green calcium and thallium-sensitive fluorescent dye.

* * * * *